United States Patent [19]

Angelsen et al.

[11] Patent Number: 4,932,415
[45] Date of Patent: Jun. 12, 1990

[54] METHOD OF COLOR CODING TWO DIMENSIONAL ULLTRASONIC DOPPLER VELOCITY IMAGES OF BLOOD FLOW ON A DISPLAY

[75] Inventors: Bjørn A. J. Angelsen, Trondheim; Kjell Kristoffersen, Oslo; Hans G. Torp, Trondheim, all of Norway

[73] Assignee: Vingmed Sound A/S, Horten, Norway

[21] Appl. No.: 270,088

[22] Filed: Nov. 14, 1988

[51] Int. Cl.⁵ ............................................. A61B 8/00
[52] U.S. Cl. ................................................ 128/661.09
[58] Field of Search ...................... 128/661.08, 661.09, 128/661.10; 73/861.25; 358/81-82; 342/181

[56] References Cited

U.S. PATENT DOCUMENTS

| | | | |
|---|---|---|---|
| 4,612,937 | 9/1986 | Miller | 128/661.09 X |
| 4,641,668 | 2/1987 | Namekawa | 128/661.09 |
| 4,719,923 | 1/1988 | Hartwell et al. | 128/661.08 |
| 4,768,515 | 9/1988 | Namekawa | 128/661.09 |
| 4,785,402 | 11/1988 | Matsuo et al. | 128/661.08 X |

*Primary Examiner*—Francis Jaworski

[57] ABSTRACT

A pulsed ultrasonic beam is swept over an image field and the backscattered signal is sampled for a multiplicity of timelags to obtain signals from a multiplicity of depths along the beam, the signals forming a two-dimensional set of range cells. A combination of the bandwidth and power of the signal from each range cell is utilized to identify those regions of the image field at which the blood velocity is sufficiently high that Doppler frequency aliasing occurs. These regions are then designated with a single color with strong contrast to the colors employed in the regions wherein the blood velocity is below this limit, so that the regions of high velocity flow are clearly delineated in the image. Where the velocity is sufficiently low that no frequency aliasing occurs, the mean Doppler shift is coded into a continuous distribution of colors for indicating the magnitude of the imaged velocities.

6 Claims, 6 Drawing Sheets

FIG. 3a NARROW BAND SIGNAL

FIG. 3b HIGHLY ALIASED SIGNAL

FIG. 3c NOISE

METHOD OF COLOR CODING TWO DIMENSIONAL ULLTRASONIC DOPPLER VELOCITY IMAGES OF BLOOD FLOW ON A DISPLAY

FIELD OF THE INVENTION

The present invention relates to the display of two-dimensional ultrasonic Doppler velocity images of blood or other fluid flow and, more particularly, to the color-coding of such information in a manner which provides the viewer with accurate and readily understandable differentiation of the various conditions and combinations of flow.

BACKGROUND OF THE INVENTION

There exist in the marketplace apparatus for presenting a color-coded two-dimensional image of a blood velocity field using noninvasive ultrasonic blood velocity measurements based on the Doppler effect. Broadly, the images are obtained by sweeping a pulsed ultrasound beam along a plane, sampling the backscattered signal for a multitude of depths and, on the basis of the Doppler shift in frequency for each such depth, estimating for each beam direction the blood velocities as a function of depth along the beam. Thus, as the beam is operatively swept across the field, a two-dimensional image of blood velocities is generated.

A first experimental instrument for two-dimensional flow imaging was presented by W. Bommer and L. Miller in 1982 ("Real Time Two Dimensional Color-Flow Doppler: Enhanced Doppler Flow Imaging in the Diagnosis of Cardiovascular Disease", 49 Am. J. Cardiology 943), and the first commercial device was developed by the Aloka Company, Ltd. of Japan (Kasai et al, "Real-Time Two-Dimensional Blood Flow Imaging Using an Autocorrelation Technique", IEEE Trans. Son. Ultras., Vol. SU-32, No. 3, May 1985, pp. 458–63). Several companies have since disclosed similar instruments such, for example, as is described in U.S. Pat. No. 4,612,937 (Miller) and German Offenlegungsschrift DE 36 37 056 A1.

The basic principles of the methodology of these prior art imaging techniques present practical limitations in the ability to represent true velocities and, in particular, to effectively distinguish betweeen laminar flow, on the one hand, and turbulent or very high velocity flows, on the other. These limitations result from inherent aspects of the methodology in that:

1. With Doppler techniques only those velocity components along the beam direction are measured; and
2. Since the beam must be pulsed to obtain spatial resolution along the beam, at high frequencies there is frequency aliasing when the Doppler shift exceeds the Nyquist limit of the sampling theorem, thus limiting the maximum flow velocity capable of measurement with this technique.

With particular respect to the latter point, if we assume that the pulse repetition frequency for the pulsed beam is $f_s$, then the Nyquist sampling theorem generally states that Doppler frequencies $f_d$ which satisfy the requirement $$|f_d| < f_s/2$$

can be measured without ambiguity. Using the complex envelope of the Doppler signal for frequency analysis, this requirement can be modified to the effect that Doppler frequencies in the range $$f_s - D < f_d < f_s + D$$

can be analyzed without ambiguity. D is an arbitrary number less than $f_s$ which can be selected as appropriate so that the interval covers the set of frequencies of interest.

The prior art imaging techniques and apparatus fail to display combinations of laminar and very high velocity or turbulent flow in a manner which satisfactorily enables a viewer to readily and accurately identify the true dynamics of the complex flows being imaged.

SUMMARY OF THE INVENTION

The present invention discloses a method of color-coding the information obtained by the Doppler shift-based measurements and for presenting the color-coded data s that all available information is displayed in the image with good color contrast between the different kinds of flow information derived from the Doppler measurements. A particularly advantageous aspect of the present invention lies in the manner in which the two-dimensional Doppler information is coded onto the screen to form a representational image of the flow velocity field. In accordance with the present invention the Doppler information is displayed using a color-coding scheme wherein laminar flow is depicted by a continuous range of colors, while turbulence or very high velocity flow is represented by a single, contrasting color so as to clearly and readily indicate to an observer those areas in which turbulent or very high velocity flow is present, and thereby enable the viewer to quickly and clearly differentiate those areas from areas of laminar flow and recognize the interrelationships between those areas.

The method of the invention employs a combination of the measured bandwidth and power of the backscattered Doppler signal to accurately determine those regions in the image at which the blood velocity is so high that Doppler frequency aliasing, yielding ambiguous velocity data, occurs. These regions are then designated in the image by a single color which strongly contrasts with the colors employed in those regions where the blood velocity is below that at which Doppler frequency aliasing occurs. In this manner, the regions of very high velocity or turbulent flow are clearly delineated in the colorcoded image.

Similarly, the measured bandwidth and the power of the backscattered Doppler signal are used to determine those regions in the image where laminar flow with no aliasing in the Doppler frequency occurs. In this case an approximate mean frequency of the Doppler signal is used as input to a continuous color scale which depicts the velocities in the laminar flow.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein similar reference characters denote similar elements throughout the several views:

FIG. 1 schematically and diagramatically illustrates various aspects of the generation of blood flow velocity information in accordance with the invention; specifically, FIG. 1a schematically depicts complex blood flow in an area being ultrasonically scanned, and FIG. 1b graphically depicts the corresponding Fourier spectrum, FIG. 1c graphically indicates the backscattered signal power, FIG. 1d graphically depicts the bandwidth, and FIG. 1e graphically illustrates the mean power of the blood in a single scanned range cell;

DETAILED DESCRIPTION OF THE PREFERRED EMBODIMENT

With particular reference to the drawings, FIG. 1 schematically depicts the application of the principle by which a color-coded image of the blood velocities in a human heart is generated. More particularly, there illustrated by way of example is a schematic representation of blood flow in a cross-section of the left heart ventricle 101 during diastole. Streamlines indicate the inflow 102 from the left atrium to the left ventricle, changing direction at the apex 103 of the left ventricle and flowing into the left ventricular outflow tract 104. Also indicated by streamlines in FIG. 1a is a jet flow 105 from a leaking aortic valve, a heart failure which is advantageously detectable in accordance with the method of the invention through strong contrast imaging with respect to the normal laminar flow of blood.

Figure 1A:
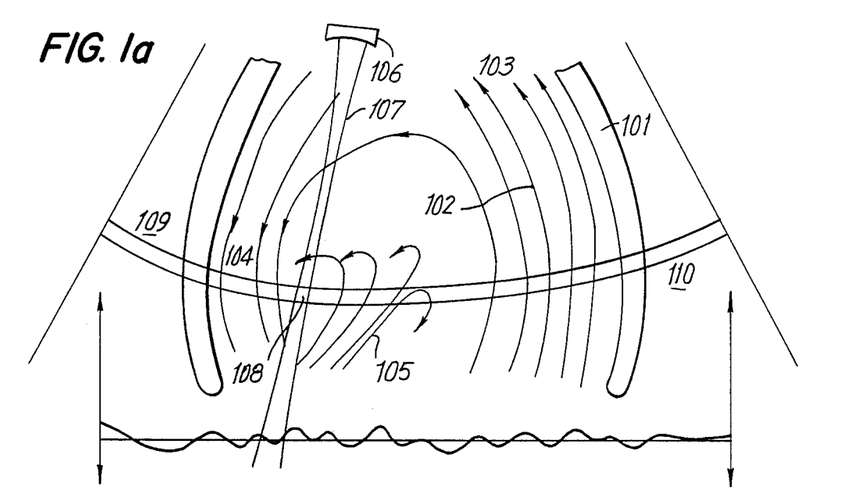

An ultrasonic transducer 106 emits a pulsed ultrasonic beam 107 into the heart. The beam can be swept over the image field either, for example, electronically using any of various known arrays, or mechanically by physically moving the transducer, all utilizing well known methods and apparatus. For ease of description and understanding, the drawings depict the situation of continuous movement of the transducer by which a continuous sectorial sweep of the ultrasonic beam is obtained. The following explanation is with respect to the signal from a single range cell 108 as the beam is swept over the image field.

Starting from the left in FIG. 1a, the range cell first passes through a region 109 of no blood flow, then enters the area 104 of laminar flow away from the transducer, next enters the region of jet flow 105, then enters the region of laminar inflow 102 (i.e. into the left ventricle from the left atrium) and, finally, leaves the left ventricle entering a region 110 of no blood flow. As should be apparent, since the ultrasonic beam is swept across the image over time, there is a direct correspondence between time and the angular direction of the ultrasonic beam.

Depicted below the heart in FIG. 1a is spectral analysis (FIG 1b) of the Doppler signal from the range cell a the transducer is scanned across the image field. Time and corresponding angular direction appear along the horizontal axis, Doppler frequency along the vertical axis, and the greyscale of the display indicates the spectral intensity of the signal. The first or leftmost portion 111 represents the spectrum of noise from the transducer and the preamplifiers of the receivers. This noise has a wide bandwidth with fairly low spectral intensity. As the range cell then enters the region 104 of laminar flow in the outflow tract, a typical narrowband spectrum 112 of high spectral intensity is obtained from the blood, overlaid on the background noise spectrum which has the same spectral intensity as at 111. As the range cell next passes into the jet flow 105 from the leaking aortic valve, the spectrum takes on the typical shape 113 of a high degree of aliasing— namely, substantially equal spectral intensity over all frequencies providing a wide bandwidth, similar to that resulting from the noise at position 111 except that the spectral intensity at the jet flow 105 is significantly higher. After this the range cell enters the region 102 of laminar inflow to the left ventricle, yielding a narrow band spectrum 114 with negative Doppler frequencies, again overlaying the basic background noise spectrum. Finally, the range cell leaves the region of flow and spectral analysis reveals noise spectrum 115 substantially identical to that seen at 111.

Figure 1B:
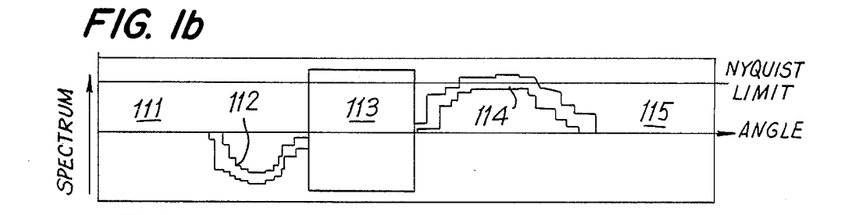
Figure 1C:
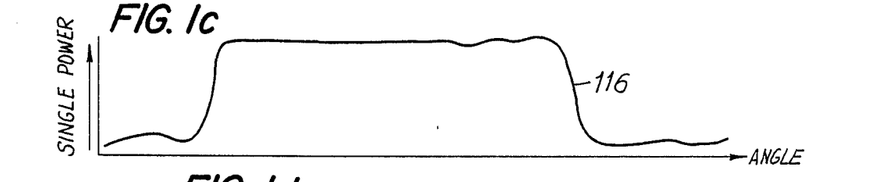
Figure 1D:
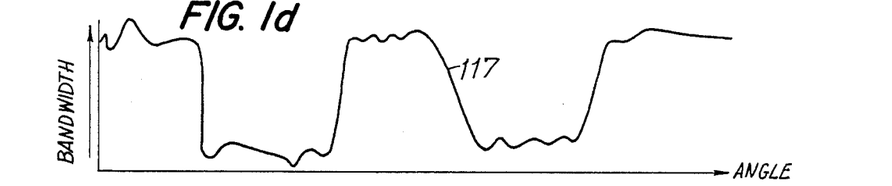
Figure 1E:
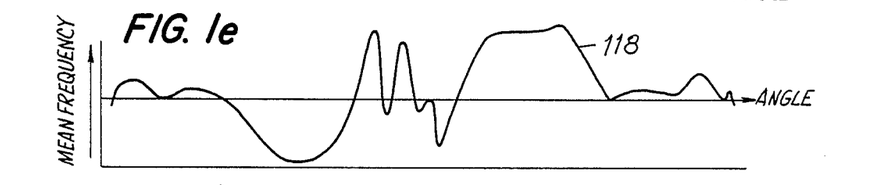

As should now be apparent, the spectral graph of FIG. 1b incorporates regions of three basic types:

1. Laminar flow of sufficiently low velocities that aliasing does not occur. The spectrum (112, 114) is narrowband with a spectral intensity higher than that of the background noise, and the mean Doppler frequency provides an approximation or estimate of blood velocity.
2. High flow velocities which result in a large degree of aliasing. The wideband spectrum (113) is similar to that for background noise, but the spectral power is higher than for noise alone. The blood velocities cannot be determined due to the aliasing, and the mean Doppler frequency does not provide meaningful information about blood velocity.
3. No signal from blood only noise. This results in a wideband spectrum (111, 115) with lowest power, and the mean frequency does not provide meaningful information about blood velocity.

These three situations can accordingly be distinguished from one another on the basis of certain characteristics of the spectrum—namely, its power and the bandwidth:

1. Laminar flow of sufficiently low velocities that aliasing does not occur: Power high and spectral bandwidth low; mean frequency used to indicate velocity.
2. High flow velocities which result in a large degree of aliasing: Power and spectral bandwidth both high.
3. No signal from the blood, only noise: Power low and spectral bandwidth high.

FIG. 1 also depicts the total signal power 116 (FIG. 1c), the spectral bandwidth 117 (FIG. 1d), and the mean frequency 118 (FIG. 1e) of the backscattered signal from the blood and noise. The additional figures clearly indicate the manner in which the different situations or combinations of flow can be distinguished by these spectral parameters.

Figure 2:
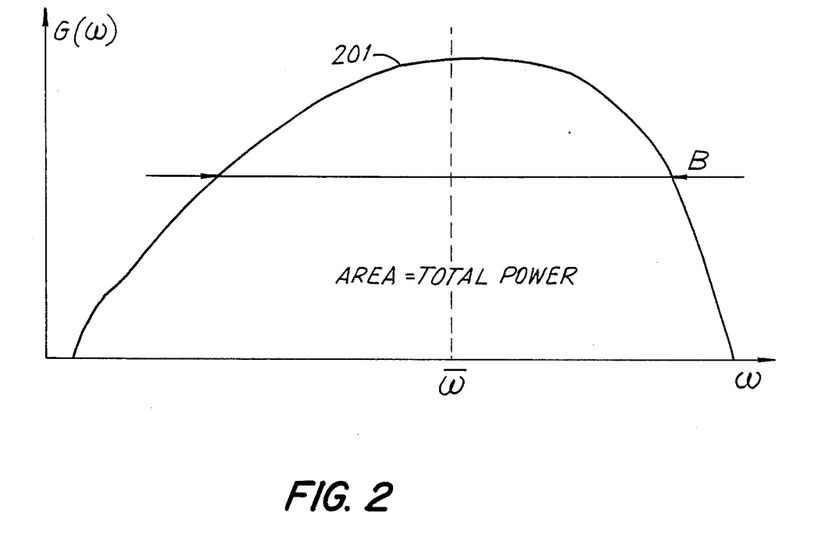
FIG. 2 graphically depicts the definition of spectra bandwidth, mean frequency, and total power based on the spectral density for a fixed time period.

A graphic definition of the spectral mean frequency, bandwidth and signal power is shown in FIG. 2. A schematic short spectrum, $G(\omega)$, is represented by the curve 201 with angular frequency along the horizontal axis and spectral intensity along the vertical axis. The angular mean frequency $\bar{\omega}$ indicates the middle of the spectrum $G(\omega)$ and can be mathematically defined as the first moment or point of gravity of the spectrum:

$$\bar{\omega} = \frac{\int d\omega \omega G(\omega)}{\int d\omega G(\omega)}$$

where the integration is taken over the entire frequency axis. As above-described with respect to FIG. 1, the mean frequency is of interest only with the narrowband spectra of laminar flow, wherein the mean frequency represents blood velocity in the range cell. It is not, therefore, critical to have the exact first moment of the spectrum; the mode or maximum value of the spectrum, or other definitions that indicate the central portion of the spectrum, may instead be employed.

The bandwidth B indicates the width of the spectrum, as shown in FIG. 2, and may for example be defined through the second moment of the spectrum:

$$B^2 = \frac{\int d\omega (\omega - \bar{\omega})^2 G(\omega)}{\int d\omega G(\omega)}$$

where, once again, the integration is taken over the entire frequency axis. As in the case of mean frequency, this precise definition of the bandwidth is not of special interest; our interest, rather, is in providing a parameter which gives an indication of spectral width.

Figure 3A:
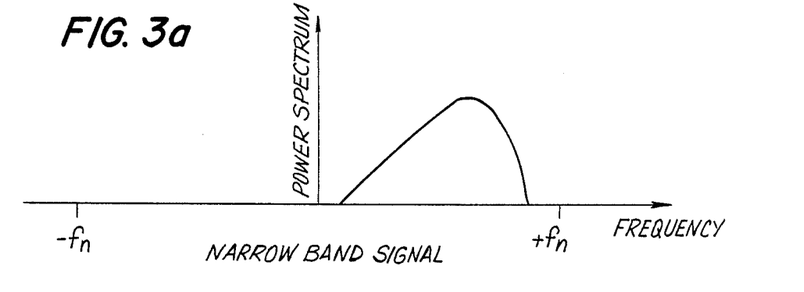
FIGS. 3a, 3b and 3c graphically depict examples of power spectra for normal laminar flow with no aliasing, for highly aliased flow, and for no signal (i.e. noise only), respectively.
Figure 3B:
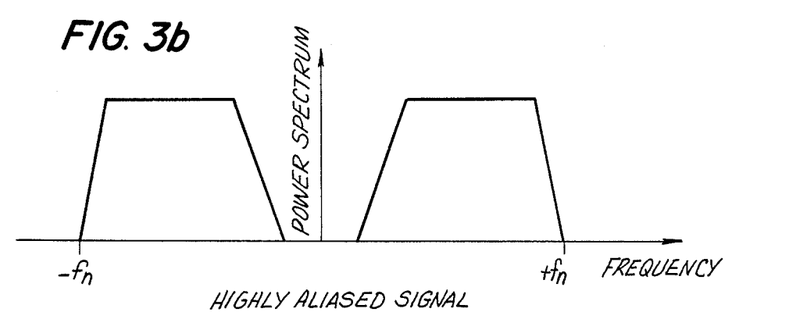
Figure 3C:
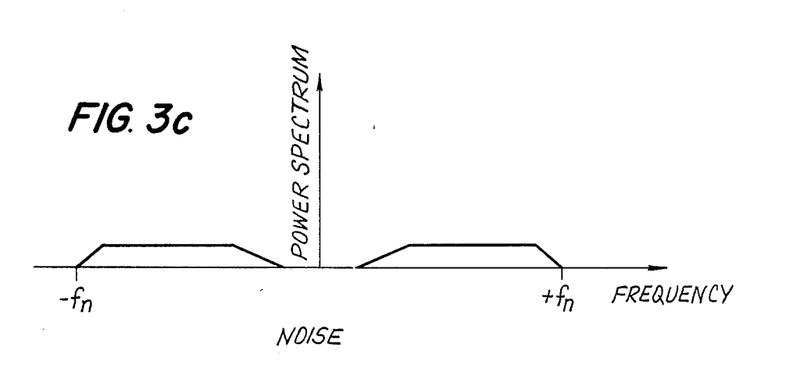

The total power of the signal is the area under the spectral curve of FIG. 2. The spectral intensity at any particular frequency is the height of the spectral curve at this frequency, this spectral intensity being displayed as the grey scale of the spectrum in FIG. 1b. Examples of the spectral power or intensity at a defined time for the three situations discussed above are illustrated in FIG. 3a which depicts laminar flow without aliasing, in FIG. 3b which depicts highly aliased flow, and in FIG. 3c which depicts the spectral power distribution of noise alone without any signal components.

Figure 4A:
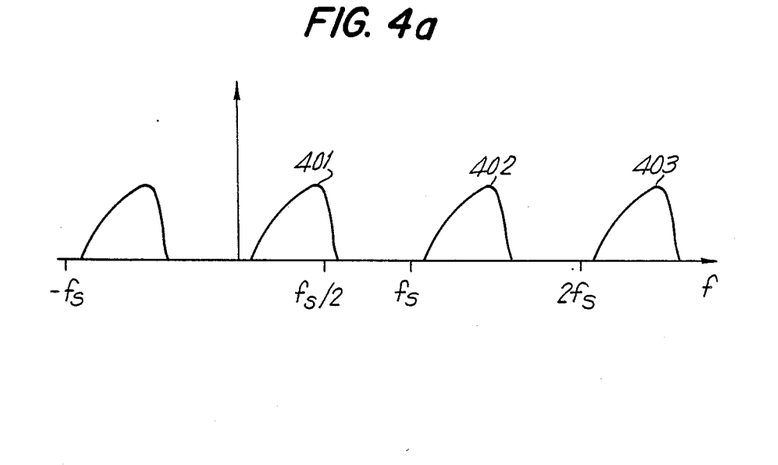
FIGS. 4a and 4b graphically illustrate the periodicity introduced in the signal spectrum from pulsing of the ultrasonic beam, and a representation of such periodicity wherein the frequency scale is folded about a circle, respectively.
Figure 4B:
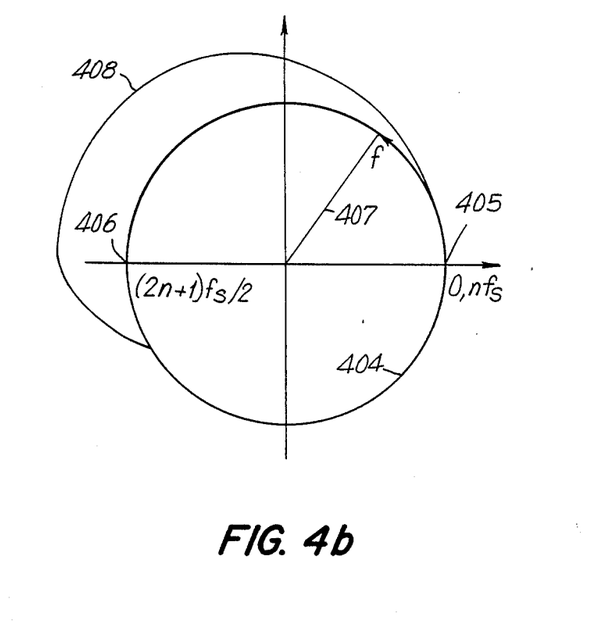

The pulsing of the ultrasonic beam introduces a periodicity of the spectrum that is seen in FIG. 4a. The figure depicts a typical spectrum 401 from laminar flow, the spectrum being repeated at multiples of the pulse repetition frequency (PRF) $f_s$, as seen at 402 and 403. FIG. 4b depicts an alternate way of illustrating this periodicity in which the entire frequency axis is wrapped about a circle 404. In FIG. 4b, zero and multiples of $f_s$, $nf_s$ lie at the intersection point 405 of the circle 404 and the right horizontal axis, whereas the intersection point 406 of the circle and the left horizontal axis corresponds to odd multiples of $f_s/2$, $(2n+1)f_s/2$.

With particular reference to the representation of FIG. 4b, starting from zero frequency at 405 and positively increasing the Doppler frequency—i.e. moving counterclockwise along the circle 404—and passing the Nyquist frequency $f_s/2$ at 406 we enter the lower half of the circle and, continuing to increase the frequency, pass the starting point 405. If, on the other hand, we start from zero at 405 with a negatively increasing Doppler frequency we move clockwise along the circle, first passing the Nyquist frequency $-f_s/2$ at 406 and, with negatively increasing Doppler shift, pass $-f_s$ at 405 and so on. For a particular frequency such, for example, as is indicated at 407 in FIG. 4b, we do not know how many times we have moved around the circle, thus introducing an ambiguity that corresponds to the periodicity of the spectrum illustrated in FIG. 4a and is a well known prediction of the Nyquist sampling theorem. The spectrum can then be shown as the curve 408 in this representation.

Thus, if we know that the frequency is increasing in the positive sense, then we have an unambiguous region from 0 to $f_s$. Similarly, if we know that the frequency is increasing in the negative sense, the unambiguous region extends from 0 to $-f_s$.

As should now be apparent, a pulsed color flow mapper can, in accordance with the invention, readily differentiate between three basic conditions or situations of blood flow—namely: (1) laminar flow without aliasing, producing a narrowband spectrum; (2) wideband Doppler signals coming either from aliasing because of high velocities or from turbulent flow with small eddies that produce both positive and negative velocities within the same range cell; and (3) noise only with no signal from the blood. These three situations can be differentiated using the bandwidth and the power of the Doppler signal and, in the case of laminar flow without aliasing, the mean Doppler frequency will provide an indication of blood velocity in the range cell. Thus, the present invention presents a method for coding the Doppler information onto a display screen so that the different conditions or situations of blood flow are displayed with strong contrast and minimal ambiguity.

In accordance with the invention, therefore, the Doppler information from the backscattered ultrasonic probe signal is treated, for the purposes of color-coded representational imaging thereof, as follows:

1. For laminar flow with a narrow bandwidth signal, the mean Doppler shift is coded in a continuous variation of colors from zero Doppler frequency past the Nyquist frequency toward the PRF of the instrument. Since there is generally a continuous spatial change in velocities, the coding advantageously enables the viewer to follow the continuous change in colors and thereby determine whether a certain color represents a frequency that has passed the Nyquist frequency in either the positive or negative direction, or its true direction is given by where it occurs relative to the Nyquist frequency. This is not, for example, the case in heretofore known color-coding schemes which present a discontinuity in the colors at the Nyquist limit making it unclear whether a color represents a positive/negative Doppler frequency above the Nyquist frequency or a negative/positive Doppler frequency below the Nyquist frequency.

2. When the blood velocity is so high that aliasing of the Doppler signal occurs, the bandwidth is high and, in accordance with the invention, a single color is employed to represent the flow. This is in contrast to currently commercially-used color scales wherein, for example, a green component proportional to the bandwidth is typically added to the existing red and blue colors producing a mosaic pattern of yellow and cyan, or of yellow and green, which does not strongly contrast with the background.

Figure 5A:
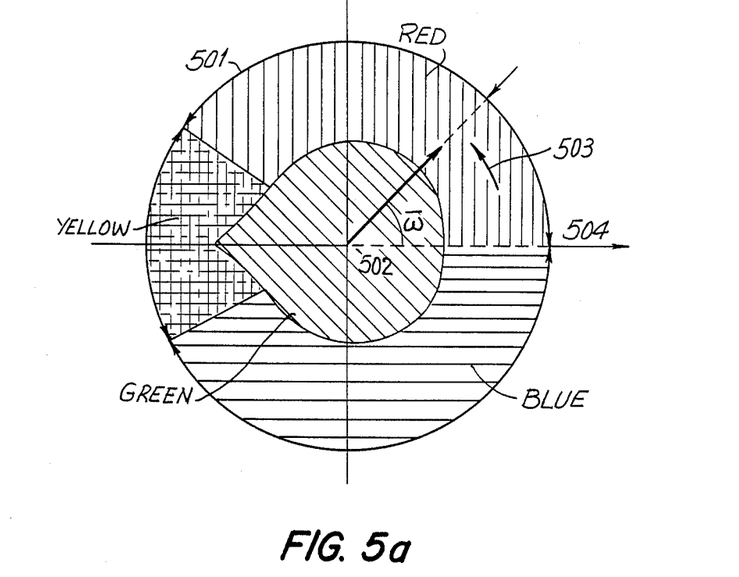
FIGS. 5a and 5b illustrate, in two alternate forms, use of the mean frequency, the bandwidth, and the power of the Doppler signal for generating a color scale in accordance with the invention.

The color scale of the invention is perhaps most clearly illustrated in the color circle of FIG. 5a. Bandwidth is on the radial axis with zero at the outer circle 501 and maximum bandwidth at the origin 502. Mean frequency is on the angular axis 503, as for example described with respect to FIG. 4b, and signal power may be represented as brightness in the colors.

A typical but nonexclusive example for low bandwidth utilizes shades of red for positively increasing frequencies starting at zero (504) on the circle, and shades of blue for negatively increasing frequencies starting at zero on the circle. The red and blue are then merged around the Nyquist frequency at 505 in a yellow, or purple, region which changes continuously from red on the upper halfcircle to blue on the lower halfcircle. As the bandwidth increases we move radially toward the origin, gradually substituting the color green for the red blue and yellow (or purple) so that in the area around the origin there appears only the color green. This single (green) color clearly and unambiguously indicates the critical area of high aliasing which may be of particular interest in the subject medical investigation.

Figure 5B:
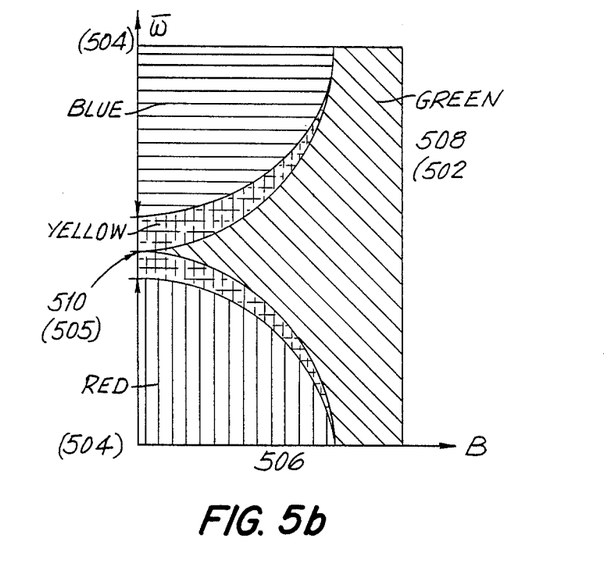

The circular color scale of FIG. 5a may alternatively be viewed in the corresponding rectangular representation of FIG. 5b wherein mean frequency is on the vertical axis 507 and bandwidth is on the horizontal axis 506. Here again, power may for example be depicted as brightness in the colors. This color scale may be thought of as cutting the circular scale of FIG. 5a from its zero point 504 to its origin 502 and then bending it open and shaping it to take the configuration of a rectangle. In any event, in FIG. 5b the low bandwidth condition is along the left vertical axis 507 and the high bandwidth condition is alon the right vertical axis 508; thus axis 508 corresponds to the origin 502 in FIG. 5a. Zero mean frequency is at the bottom, increasing positively upwards, passing the Nyquist frequency 510 in the center and terminating at $f_s$ at the top, thus corresponding to counterclockwise movement along the circular scale of FIG. 5a. Negative frequencies start at zero on the top of axis 508 and move downward toward $-f_s$ at the bottom, thus corresponding to clockwise movement along the circular scale. The corresponding points 502, 504 and 505 of FIG. 5a are depicted in parentheses at their respective corresponding positions in FIG. 5b.

There are many known methods of calculating the mean frequency, bandwidth and power of the Doppler signal and, as hereinabove mentioned, only close or relative representations rather than exact calculations of these parameters are needed in accordance with the invention. Since these parameters are estimates over a limited time, they will have a random error; it may therefore be advantageous to use parameters which do not exactly represent the mean frequency, bandwidth and power, but, instead, have a smaller estimation uncertainty than parameters which provide a more exact representation thereof.

A practical and currently preferred method of estimating these three parameters is to use the autocorrelation function for the complex envelope of the Doppler signal for zero lag and for the lag between two immediately adjacent or neighboring pulses. The real and imaginary parts of the complex envelope are obtained by quadrature demodulation of the RF signal in a known manner. The autocorrelation function of the complex envelope is illustrated in the complex plane in FIG. 6 wherein 601 denotes the real axis and 602 the imaginary axis. The autocorrelation function for zero lag, R(0), is indicated by the arrow 603, and the autocorrelation function with a lag of the distance between two ultrasound pulses, R(1), is indicated by the arrow 604. The amplitude of R(0) is utilized as an estimate for the power of the signal, and the argument 605 of R(1) is utillized as an estimate of mean frequency. The difference 606 in amplitude of the autocorrelation function at zero lag and at unity lag forms the basis of an estimate of the signal bandwidth since the length 606 is proportional to $B^2R(0)$.

Figure 6:
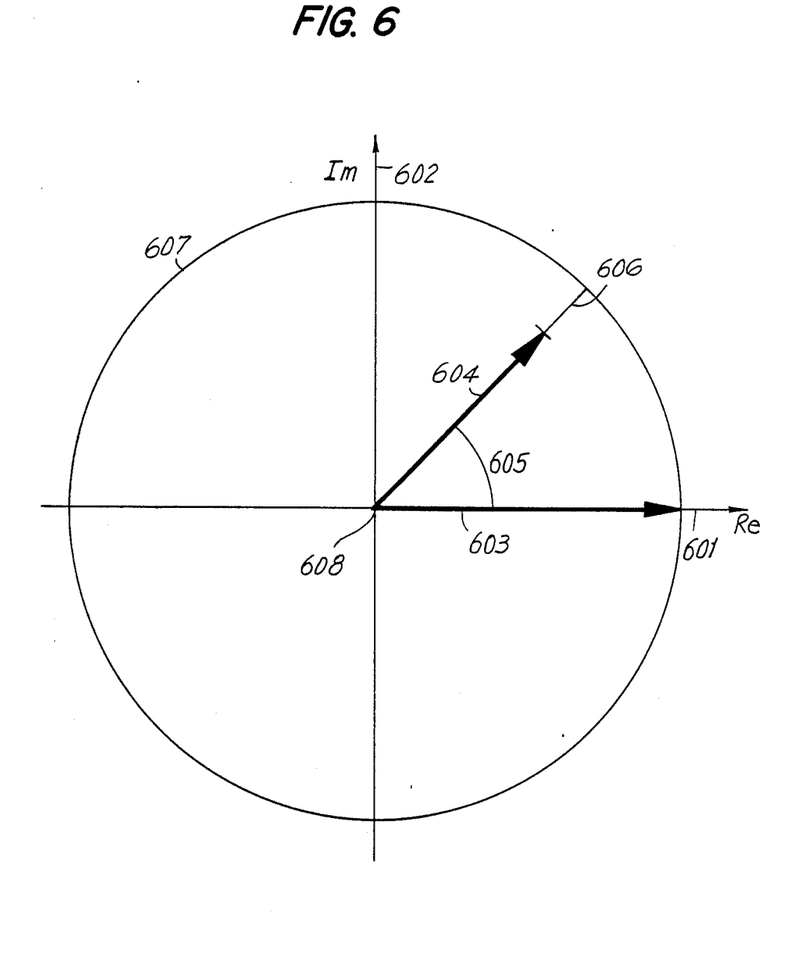
FIG. 6 depicts the manner in which estimates of the mean frequency, the bandwidth, and the power of the backscattered signal from a single range cell may be obtained from the autocorrelation function of the complex envelope of the Doppler signal for zero and unity lag.

This complex representation of the autocorrelation function has a similarity to the circular color scale of FIG. 5a in that, for small bandwidths, the amplitude of R(1) is close to the amplitude of R(0). With small bandwidths, R(1) will rotate close to the circle 607 and through R(0), while with large bandwidths, R(1) will be close to the origin 608. We can therefore let the normalized complex autocorrelation function $\rho(1) = R(1)/R(0)$ directly define the color in FIG. 5a, where the circle 501 now represents the unit circle in the complex plane for $\rho(1)$.

While there have been shown and described and pointed out fundamental novel features of the invention as applied to a currently preferred embodiment thereof, it will be understood that various omissions and substitutions and changes in the form and details of the disclosed method may be made by those skilled in the art without departing from the spirit of the invention. It is the intention, therefore, to be limited only as indicated by the scope of the claims appended hereto.

What is claimed is:

1. A method for color-coded imaging of blood flow velocities in a field onto a display, comprising the steps of:

scanning an ultrasonic beam pulsed at a pulse repetition frequency across the field to provide a Dopplershifted backscattered signal from a discrete set of range cells in the field;

sampling the backscattered signal from the range cells along the beam;

estimating predetermined parameters from the backscattered signal from each range cell, said parameters comprising the mean frequency, the power and the bandwidth of the backscattered signal;

assigning, on the basis of said parameters, predetermined colors for imaging the blood flow velocities on the display, such that for low bandwidth, the mean frequency is assigned to a range of selected first colors which are predeterminately varied as the mean frequency varies, in both the positive and negative sense, from zero frequency to the pulse repetition frequency of the beam, and for increasing bandwidth said first colors are gradually replaced with a single second color until, at large bandwidths, only said single second color is assigned to the display, said single second color being selected to strongly contrast with said first colors; and mapping the assigned colors for both positive and negative mean frequencies onto the display, whereby the displayed image presents the full range of blood flow velocities in the field such that different flow conditions ma be readily distinguished.

2. A method in accordance with claim 1 wherein said color assigning step further comprises varying the brightness of said assigned first and second colors in accordance with the power of the backscattered signal.

3. A method in accordance with claim 1, wherein the mean frequency is assigned, for low bandwidth, to a continuous range of said first colors.

4. A method in accordance with claim 1, wherein said second color is green, and said first colors are red, yellow and blue, said first colors being mixed around the Nyquist frequency so as to provide in the display image a substantially continuous variation in color with corresponding variations in the mean frequency.

5. A method in accordance with claim 1, wherein said estimating step comprises estimating the autocorrelation function of the complex Doppler backscattered signal for zero lag and for the lag of the temporal distance between pulses of the ultrasonic beam.

6. A method in accordance with claim 1, wherein said second color is green, and said first colors are red, purple and blue, said first colors being mixed around the Nyquist frequency so as to provide in the display image a substantially continuous variation in color with corresponding variations in the mean frequency.

* * * * *